US00PP34275P2

(12) United States Plant Patent
Hansen

(10) Patent No.: US PP34,275 P2
(45) Date of Patent: May 31, 2022

(54) ***CLEMATIS* PLANT NAMED 'STAND BY ME LAVENDER'**

(50) Latin Name: ***Clematis* hybrid**
Varietal Denomination: Stand by Me Lavender

(71) Applicant: Hans A Hansen, Zeeland, MI (US)

(72) Inventor: Hans A Hansen, Zeeland, MI (US)

(73) Assignee: Walters Gardens, Inc., Zeeland, MI (US)

( * ) Notice: Subject to any disclaimer, the term of this patent is extended or adjusted under 35 U.S.C. 154(b) by 0 days.

(21) Appl. No.: 17/300,865

(22) Filed: Nov. 29, 2021

(51) Int. Cl.
*A01H 5/02* (2018.01)
*A01H 6/72* (2018.01)

(52) U.S. Cl.
USPC ..... Plt./228
CPC ..... *A01H 6/72* (2018.05)

(58) Field of Classification Search
USPC ..... Plt./228
CPC ..... A01H 6/72; A01H 5/02
See application file for complete search history.

*Primary Examiner* — Keith O. Robinson

(57) ABSTRACT

The new hybrid plant of *Clematis* 'Stand by Me Lavender' of short, compact, upright habit with support, with ovate foliage and dark purple buds producing nodding flowers with typically four reflexed tepals of lavender-purple beginning late May and reblooming through late summer on upright non-vining stems.

1 Drawing Sheet

Botanical denomination: *Clematis* hybrid.
Cultivar designation: 'Stand by Me Lavender'.

STATEMENT REGARDING PRIOR DISCLOSURES UNDER 37 CFR 1.77(B)(6)

The first public disclosure of the claimed plant, in the form of a sale, was made by Walters Gardens, Inc. on Sep. 27, 2021 to Corso's Flower Farm, Romance Gardens, Weakland Greenhouse and Baileys Nursery. Prior to that, on Dec. 1, 2020 the claimed plant was displayed with a non-enabling photograph and brief description in a website operated by Walters Gardens, Inc., and on May 21, 2021 as a non-enabling photograph and brief description in the 2020-2021 Catalog by Walters Gardens, Inc., who obtained the plant and all information relating thereto, from the inventor. No plants of *Clematis* 'Stand by Me Lavender' have been sold, in this country or anywhere in the world, nor has any disclosure of the new plant been made more than one year prior the filing date of this application, and such sale or disclosure within one year was either derived directly or indirectly from the inventor.

BACKGROUND OF THE INVENTION

The present invention relates to a new and distinct plant of bush-type *Clematis*. The seed producing the new plant was collected by the inventor from a research garden bed at a wholesale nursery in Zeeland, Mich., USA on Aug. 27, 2014. The seed was from a selected, 'Stand by Me' U.S. Plant Pat. No. 30,556 as the female parent, times 'Rose Colored Glasses' (not patented) as the male parent. The new plant passed the original evaluation in summer of 2016 at a wholesale perennial nursery in Zeeland, Mich., USA and was the subject of the subsequent further evaluations and given the breeder code 14-129-1 during these trials. The new plant was selected from among many other seedlings growing at the same nursery in Zeeland, Mich. which met the rigorous criteria of excellent foliage and habit established as breeding goals.

'Stand by Me Lavender' has been asexually propagated since 2016 by shoot tip cuttings at the same nursery in Zeeland, Mich. The resultant asexually propagated plants have remained stable and exhibit the identical characteristics as the original plant in successive generations.

BRIEF SUMMARY OF THE INVENTION

'Stand by Me Lavender' differs from all other *Clematis* known to the applicant. The nearest known cultivars are *Clematis* 'Center Star' U.S. Plant Pat. No. 17,010, 'New Love' U.S. Plant Pat. No. 13,977 and 'Stand by Me' U.S. Plant Pat. No. 30,556. 'Center Star' is slightly taller than the new plant, the flowers are more upright, less drooping with typically five tepals that are less recurved and more purple in color. 'New Love' is shorter in habit and has lighter-colored, outwardly, verticillate flowers. 'Stand by Me' has a taller and denser habit with foliage having a purplish bronze cast to the back of the foliage when young and violet-blue tepals.

The female parent is more dense with violet-blue flowers. The male parent has pink flowers with foliage that is longer, lighter green and narrower without the bronze on the underside. The new plant is more vigorous than both the parents.

The new plant, 'Stand by Me Lavender', differs from all *Clematis* known to the inventor in the following combined traits:

1. The foliage is ovate and micro-tomentose below and glabrous above;
2. Multiple nodding flowers per node begin in late May to June with rebloom in the late summer typically having four tepals per flower;
3. Flowers of reflexed lavender-purple tepals develop from dark purple buds;

4. Plant habit is generally short, compact, upright and non-vining but benefits from stakes or other nearby plants when mature.

BRIEF DESCRIPTION OF THE DRAWINGS

The photographs of the new plant demonstrate the overall appearance of trial garden at a wholesale perennial nursery in Zeeland, Mich., USA. The colors are as accurate as reasonably possible with color reproductions. Some slight variation of color may occur as a result of lighting quality, intensity, wavelength, and direction or reflection.

DETAILED BOTANICAL DESCRIPTION

Figure 1:
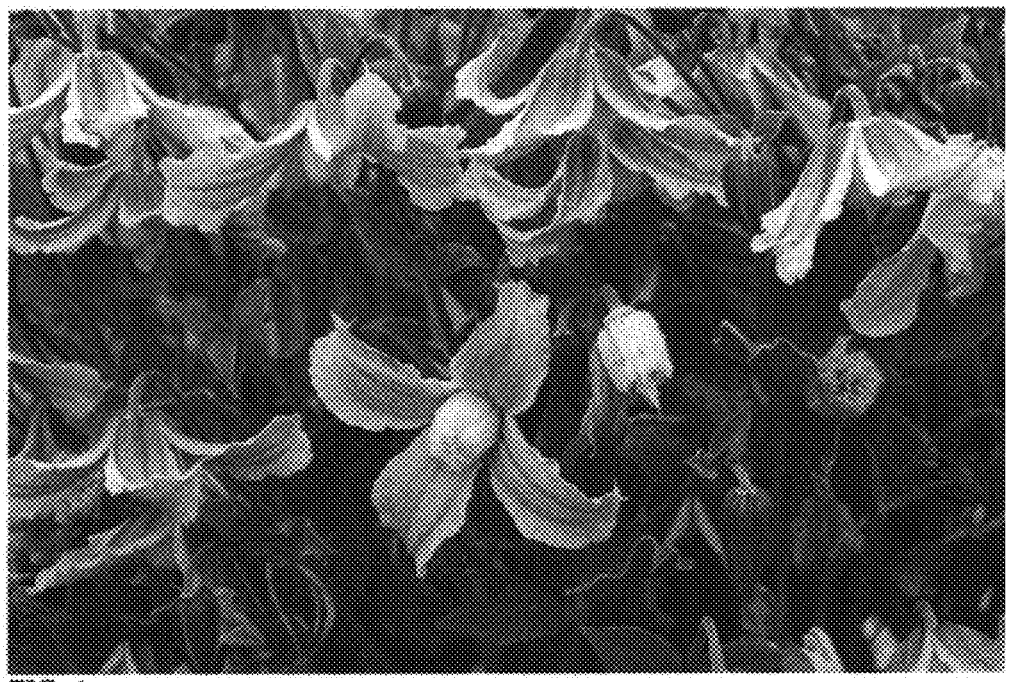
FIG. 1 a close-up of the flowers from a side view.
Figure 2:
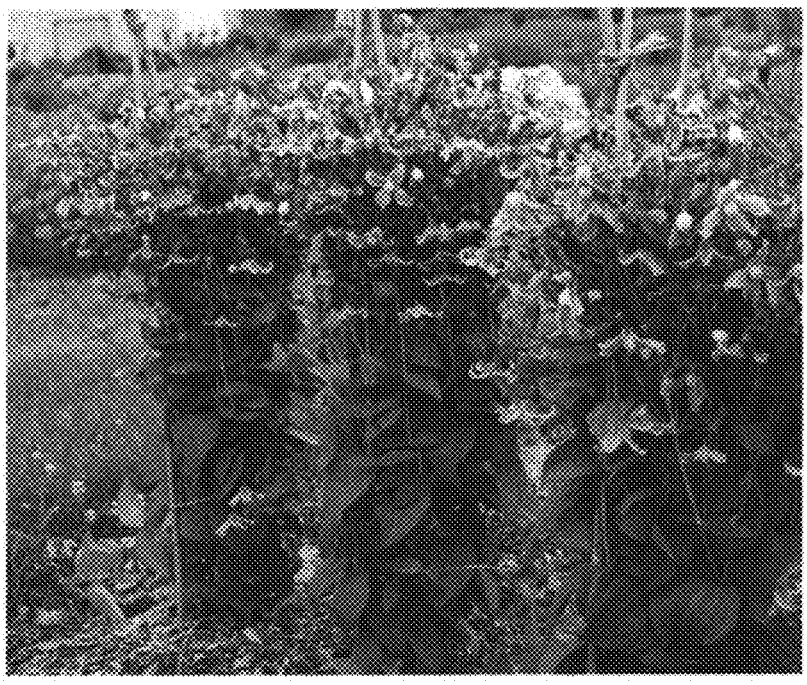
FIG. 2 shows the habit of some three-year-old plants in early season flowering showing flowering habit and attitude.

The following description is based on a three-year-old plant growing in a full-sun trial garden with supplemental water and fertilizer at a wholesale perennial nursery in Zeeland, Mich., USA. The new plant has not been grown under all possible environments and may phenotypically appear different under different conditions such as light, temperatures, fertilizer, and water, without any difference in genotype. The color descriptions are from the 2015 edition of The Royal Horticultural Society Colour Chart except where common dictionary terms are used.

Parentage: The female (seed parent) is 'Stand by Me'; the male (pollen parent) is 'Rose Colored Glasses';

Plant habit: Winter-hardy, non-vining, herbaceous perennial of semi-woody stems producing upright habit with support, dying to the ground each winter; flowering on current year's growth only; to about 89.0 cm tall in flower and spreading to about 90.0 cm across about 25.0 cm above soil; foliage to about 82.0 cm tall;

Roots: Coarse, branched; tan to light brown in color depending on soil type; RHS 158A to RHS 161C;

Growth rate: Rapid, finishing in four-liter container in about 8 to 10 weeks from a one-year-old vernalized plant;

Stems: To about 60 per plant; cylindrical with longitudinal carina; glabrous proximally and micro-puberulent distally; branched in upper nodes; to about 83.0 cm long and 4.0 mm diameter at base; flowering in upper 30.0 cm;

Stem color: Proximally carina nearest RHS 166A and furrows between RHS 164A and RHS 166B, distally nearest RHS 146D with carina nearest RHS N186C;

Branches: At about 60 degrees above horizontal; variable length to about 75 cm long;

Internode: About 7 to 9 per stems to 5.0 mm across;

Internode color: Variable, between RHS 145A in lower light and RHS N186B in high light intensity;

Foliage: Opposite; simple; ovate; apex acute; base rounded, sessile and partially clasping; margin entire; minutely tomentose abaxial and glabrous adaxial; newly expanded foliage is upright with young opposite leaves nearly enclosing meristem, maturing to flat and horizontal;

Leaf blade size: Variable, to about 11.0 cm long and about 6.0 cm wide in middle; adaxial slightly lustrous when young emerging, average about 9.26 cm long and 5.3 cm wide;

Leaf color: Proximal mature leaves adaxial surface nearest RHS 137B, abaxial surface nearest RHS 146B; young emerging leaves adaxial surface nearest RHS 138A with light to moderate bronze blushing of nearest RHS 187A, abaxial surface between RHS 146C and RHS 146D with moderate bronze blushing of nearest RHS 187A;

Petiole: Sessile;

Veins: Palmate-penta-nerved to multi-costate; convergent; glabrous adaxial, micro-tomentose abaxial;

Vein color: Adaxial mature leaves between RHS 146A and RHS 137B; abaxial mature leaves in nearest RHS 147C; adaxial young leaves in between RHS 137B and RHS 147C; abaxial young leaves nearest 146C;

Inflorescence: Flowers solitary; at nodes; flowering portion about 30.0 cm long;

Flower attitude: Buds upright, flowers drooping to downwardly when mature;

Flower fragrance: None detected;

Flower period: Late May to June with rebloom into late summer; individual flowers remaining effective in flower for about 6 to 8 days;

Peduncle: Cylindrical; micro-puberulent; to about 7.5 cm long and 2.0 mm in diameter, average 5.5 cm long and 1.5 mm diameter;

Peduncle attitude: Attitude upright becoming drooping to downwardly distally;

Peduncle color: Variable; on older flowers and young buds nearest RHS 187A distally, proximally nearest RHS 146D with ridges of nearest RHS 87A;

Buds one day prior to opening: Conical with narrowly acute apex, and rounded base; glabrous with carina along tepal unions tomentose; with apex pointing downwardly; about 22.0 mm long and 9.0 mm diameter;

Bud color: Basal one-third between RHS 83B and RHS 83A transitioning to nearest RHS 83D at apex;

Flower: Single; solitary; perfect; incomplete; campanulate, cruciform; actinomorphic; about 5.0 cm across at tepal apices and 1.5 cm deep;

Flower angle: Outwardly at initial anthesis becoming drooping to downwardly within 2 days of anthesis;

Tepals: Typically four in two identical sets; lanceolate; acute apex; truncate base; recurved; tri-nerved with midrib and one pair of main veins; margins entire, becoming slightly involute; distal one-half of margin erosulate; adaxial glabrous and matte; micro-puberulent abaxial between outer main vein and margin, glabrous and matte between outer main veins and midrib; about 40.0 mm long and 12.0 mm wide in middle; self-cleaning;

Tepal color: Adaxial between RHS N87D and RHS N87C in longitudinal center and proximally, distally nearest RHS N87C in reflexed portion; abaxial center proximally nearest RHS 86A lightening to nearest RHS 86C distally, margin between outer main vein and margin nearest RHS 85A;

Petals and sepals: Not present;

Androecium: About 60; flattened dorsa-ventrally, abaxial pubescent distal half, glabrous proximal half; total 14.0 mm long and 2.0 mm wide;

*Filaments*.—Flattened; pubescent abaxial, glabrous adaxial, margin ciliate; about 10.0 mm long and 2.0 mm wide and about 0.2 mm thick; color nearest RHS 4D.

*Anthers*.—Basifixed; longitudinal; ellipsoidal; pubescent abaxial; introrse; to about 3.0 mm long and 1.2 mm diameter, decreasing toward flower axis; color nearest RHS 11D.

*Pollen*.—Abundant; powdery; color nearest RHS 11D.

Gynoecium: About 60 internal to androecium; to 12.0 mm long;

*Style*.—Terete to tapered; about 8.0 mm long and 0.8 mm diameter; pilose to sericeous; color nearest RHS 138B covered in silvery hairs.

*Stigma*.—Ellipsoidal; about 3.0 mm long and 0.5 mm diameter; color nearest RHS 155A.

*Torus*.—Semi-dome shaped; about 4.0 mm diameter across at base and 3.0 mm tall; color as developing nearest RHS 157A, at maturity with seeds removed nearest RHS N199B.

Reproductive structures:

*Fruit*.—Produced in globose plumose head, to about 5.0 cm diameter and 5.0 cm tall; seeds with plumose tails curved around equal distance above and below torus.

*Seed*.—About 50 to 60 per head; flattened achene with style persistent as plumose tail; hairs adpressed becoming antrorse as maturing and at nearly 90 degree angle to style when mature, extending 3.0 mm long; tail portion to 48.0 mm long; pubescent achene base 4.0 mm long, 4.0 mm wide and 1.0 mm thick; color shortly as developing plumose feather tail variable nearest RHS 189D and RHS N87A with hairs nearest RHS 198D, achene base center nearest RHS 146B and outside margins between RHS 146D and RHS 145A; color when mature plumose feather tail nearest RHS N199B with hairs nearest RHS 164C, achene base variable some nearest RHS 165B and others nearest RHS 165A.

Culture: *Clematis* 'Stand by Me Lavender' grows best in full sun with ample moisture, good drainage and mulch. The new plant is cold hardy from USDA zones 3 to at least zone 8.

Disease and pest tolerance: Pest and disease resistance and tolerance outside of that normal for *Clematis* is not known at this time.

It is claimed:

1. The new and distinct ornamental *Clematis* plant named 'Stand by Me Lavender' as herein described and illustrated.

* * * * *